(12) United States Patent
Jorneus et al.

(10) Patent No.: US 9,615,894 B2
(45) Date of Patent: Apr. 11, 2017

(54) COMPONENTS FOR GUIDED THREADING OF BONE

(71) Applicant: Nobel Biocare Services AG, Kloten (CH)

(72) Inventors: Lars Jorneus, Frillesas (SE); Henrik Petersson, Zurich (CH)

(73) Assignee: Nobel Biocare Services AG, Kloten (CH)

( * ) Notice: Subject to any disclaimer, the term of this patent is extended or adjusted under 35 U.S.C. 154(b) by 0 days.

(21) Appl. No.: 14/954,183

(22) Filed: Nov. 30, 2015

(65) Prior Publication Data

US 2016/0135920 A1    May 19, 2016

Related U.S. Application Data

(63) Continuation of application No. 13/394,524, filed as application No. PCT/EP2010/005448 on Sep. 6, 2010, now abandoned.

(30) Foreign Application Priority Data

Sep. 7, 2009    (EP) .................................... 09011434

(51) Int. Cl.
  *A61F 2/08*    (2006.01)
  *A61C 1/08*    (2006.01)
  (Continued)

(52) U.S. Cl.
  CPC .......... *A61C 1/084* (2013.01); *A61B 17/1655* (2013.01); *A61B 17/176* (2013.01); *A61C 8/0022* (2013.01); *A61C 8/0089* (2013.01)

(58) Field of Classification Search
  CPC ........................ A61B 17/1655; A61B 17/1673
  (Continued)

(56) References Cited

U.S. PATENT DOCUMENTS 5,489,307 A    2/1996 Kuslich et al.
5,593,410 A    1/1997 Vrespa
(Continued)

FOREIGN PATENT DOCUMENTS

DE    27 44 564    4/1979
EP    1 759 658    3/2007
(Continued)

OTHER PUBLICATIONS

International Search Report for Application No. PCT/EP2010/005448 (the PCT counterpart of U.S. Appl. No. 13/394,524) mailed on Dec. 21, 2010 in 4 pages.
(Continued)

*Primary Examiner* — Matthew Lawson
(74) *Attorney, Agent, or Firm* — Knobbe, Martens, Olson & Bear LLP

(57) ABSTRACT

A combination of a guide sleeve for a surgical template, a drill, and a thread forming tool is disclosed. The guide sleeve has a guide surface for guiding the thread forming tool. The drill has at least one cutting edge for cutting a recess in bone. The thread forming tool has a thread forming section for forming at least one thread in bone, and a guide section for guidance by the guide surface of the guide sleeve, the thread forming section comprising an apical portion, and a coronal portion. A maximum diameter of the apical portion of the thread forming section is smaller than or equal to a maximum diameter of the cutting edge of the drill.

19 Claims, 9 Drawing Sheets

(51) Int. Cl.
*A61B 17/16* (2006.01)
*A61B 17/17* (2006.01)
*A61C 8/00* (2006.01)

(58) Field of Classification Search
USPC .......................................... 606/300–321, 104
See application file for complete search history.

(56) References Cited

U.S. PATENT DOCUMENTS

| | | | |
|---|---|---|---|
| 5,643,269 | A | 7/1997 | Härle |
| 5,741,267 | A | 4/1998 | Jorneus et al. |
| 6,086,595 | A | 7/2000 | Yonemura et al. |
| 6,120,506 | A * | 9/2000 | Kohrs ................ A61B 17/1671 606/79 |
| 6,196,842 | B1 | 3/2001 | Jorneus |
| 6,283,966 | B1 | 9/2001 | Houfburg |
| 6,863,529 | B2 | 3/2005 | Strong et al. |
| 6,896,517 | B1 | 5/2005 | Bjorn et al. |
| 7,008,228 | B2 | 3/2006 | Bjorn et al. |
| 7,175,435 | B2 | 2/2007 | Andersson et al. |
| 7,247,020 | B2 | 7/2007 | Takahashi et al. |
| 7,572,125 | B2 | 8/2009 | Brajnovic |
| 7,597,557 | B2 | 10/2009 | Fromovich et al. |
| 7,621,916 | B2 | 11/2009 | Lauryssen et al. |
| 7,845,946 | B2 | 12/2010 | Brajnovic |
| 7,950,924 | B2 | 5/2011 | Brajnovic |
| 8,142,189 | B2 | 3/2012 | Brajnovic |
| 8,157,563 | B2 | 4/2012 | Brajnovic |
| 8,186,999 | B2 | 5/2012 | Andersson et al. |
| 8,740,912 | B2 | 6/2014 | Stark |
| 2002/0022862 | A1 | 2/2002 | Grafton et al. |
| 2002/0116006 | A1 | 8/2002 | Cohen |
| 2002/0138079 | A1 | 9/2002 | Cohen |
| 2004/0082956 | A1 * | 4/2004 | Baldwin ............ A61B 17/0401 606/232 |
| 2004/0260291 | A1 | 12/2004 | Jensen |
| 2005/0026114 | A1 | 2/2005 | Nilo et al. |
| 2006/0008763 | A1 | 1/2006 | Brajnovic |
| 2006/0008770 | A1 | 1/2006 | Brajnovic et al. |
| 2006/0079894 | A1 | 4/2006 | Colleran et al. |
| 2007/0093837 | A1 | 4/2007 | Bohrmann et al. |
| 2007/0099153 | A1 | 5/2007 | Fromovich |
| 2007/0293867 | A1 | 12/2007 | Anitua |
| 2008/0038692 | A1 | 2/2008 | Andersson et al. |
| 2008/0118895 | A1 | 5/2008 | Brajnovic |
| 2008/0153065 | A1 | 6/2008 | Brajnovic et al. |
| 2008/0261175 | A1 | 10/2008 | Hurson |
| 2009/0136898 | A1 | 5/2009 | Kim |
| 2009/0239197 | A1 | 9/2009 | Brajnovic |
| 2009/0253097 | A1 | 10/2009 | Brajnovic |
| 2010/0009314 | A1 | 1/2010 | Tardieu et al. |
| 2010/0062389 | A1 | 3/2010 | Drews et al. |
| 2011/0008751 | A1 | 1/2011 | Pettersson |
| 2012/0123576 | A1 | 5/2012 | Pettersson et al. |
| 2012/0191097 | A1 | 7/2012 | Jorneus et al. |
| 2012/0191103 | A1 | 7/2012 | Jorneus et al. |

FOREIGN PATENT DOCUMENTS

| | | |
|---|---|---|
| FR | 2 735 008 | 12/1996 |
| WO | WO 2004/103202 | 12/2004 |
| WO | WO 2005/011514 A2 | 2/2005 |
| WO | WO 2006/014130 | 2/2006 |
| WO | WO 2008/128757 | 10/2008 |
| WO | WO 2011/026644 | 3/2011 |

OTHER PUBLICATIONS

International Preliminary Report on Patentability for Application No. PCT/EP2010/005448 (the PCT counterpart of U.S. Appl. No. 13/394,524) issued Mar. 13, 2012 in 8 pages.

International Search Report for Application No. PCT/EP2010/005449 (the PCT counterpart of U.S. Appl. No. 13/394,532) mailed on Mar. 23, 2011 in 6 pages.

International Preliminary Report on Patentability for Application No. PCT/EP2010/005449 (the PCT counterpart of U.S. Appl. No. 13/394,532) issued Mar. 13, 2012 in 8 pages.

Dentsply Friadent: "XiVE—ExpertEase Chirurgie Step-by-Step", Mar. 19, 2009 (cited on International Search Report for PCT/EP2010/005449; submitted 6 pages retrieved from http://www.dentsply-friadent.com/downloads on Feb. 14, 2012).

* cited by examiner

US 9,615,894 B2

COMPONENTS FOR GUIDED THREADING OF BONE

CROSS-REFERENCE TO RELATED APPLICATIONS

This application is a continuation application of U.S. patent application Ser. No. 13/394,524, filed Apr. 12, 2012, which is a national stage application under 35 U.S.C. §371 of PCT Application No. PCT/EP2010/005448, filed on Sep. 6, 2010, which published in English as WO 2011/026643 A1 on Mar. 10, 2011 and which claims priority benefit of European Patent Application No. 09011434.9, filed on Sep. 7, 2009. The disclosure of PCT/EP2010/005448 is herein incorporated by reference in its entirety.

BACKGROUND

Field of the Invention

This invention pertains in general to the field of implant surgery. More particularly, the invention relates to a combination of components for guided threading of bone, wherein a guide sleeve may guide a drill for the formation of a recess in bone as well as a thread forming tool for forming threads in the recess. Also, the guide sleeve may guide installation of an implant in the recess to a pre-planned position. The guide sleeve may be part of a surgical template, for example planned using a computer implemented planning software.

Description of the Related Art

Surgical templates for placement of implants to a preplanned position may be used for improved accuracy and security of the final position of the implant in the bone of the patient. The surgical template may also be used to guide a drill for forming a recess in the bone. One example of such drill and implant guided surgery is for placement of oral and/or cranio-maxillofacial implants, such as implants in a jawbone, and is available under the NobelGuide™ planning and treatment concept from Nobel Biocare®.

In certain clinical applications when the implant is placed, such as placement in a jawbone, the implant has a tendency to deviate from the drilled hole, for example due to varying density of the bone surrounding the implant, both in the vertical as well as the horizontal direction of the implant. If, for example, the bone is denser on one side of the central longitudinal axis of the implant, it will often deviate towards the softer bone, and end up in a non-optimal position, which is different from a planned position. If this happens during guided surgery, the implant mount, which is guided by a guide sleeve of the surgical template, may jam in the guide sleeve.

Furthermore, most implant types are wider at the coronal end than at the apical end. The increase in width from the apical to the coronal end can be of two types, a) a substantially cylindrical implant with a wider coronal platform, or b) a tapered implant tapering from its apical end at least partially towards its coronal end. For both types of implants it is difficult to provide guidance between the implant mount and the surgical template, since there is sometimes not enough space available, such as in the oral cavity, to make the distance from the bone to the coronal end of the guide sleeve long enough. As a consequence, guidance between the implant mount and the surgical template is not provided during the initial placement of the implant in the bone but only during the final seating of the implant. This may lead to deviations of the implant from its planned position as the implant starts generating threads before the implant mount is guided, which in turn may lead to stresses in the surgical template without the possibility to end up in the planned position. Since often several implants are placed using a single surgical template, a deviation of one implant inevitably affects the possibility to place another implant in its planned position, such as if the entire surgical template has moved from its accurate position relative to the bone of the patient.

Hence, an improved combination of components for placement of an implant through a guide sleeve of a surgical template would be advantageous and in particular allowing for improved precision, increased flexibility, cost-effectiveness, and/or patient safety would be advantageous.

SUMMARY

Accordingly, certain embodiments of the present disclosure preferably seek to mitigate, alleviate or eliminate one or more deficiencies, disadvantages or issues in the art, such as the above-identified, singly or in any combination by providing a combination of components for guided placement of an implant according to the appended patent claims.

According to a first aspect of certain embodiments, a combination comprises a guide sleeve for a surgical template, a drill, and a thread forming tool. For example, the guide sleeve has a guide surface for guiding the thread forming tool. The drill has at least one cutting edge for cutting a recess in bone. The thread forming tool has a thread forming section for forming at least one thread in bone, and a guide section for guidance by the guide surface of the guide sleeve, the thread forming section comprising an apical portion, and a coronal portion. In certain embodiments, a maximum diameter of the apical portion of the thread forming section is smaller than or equal to a maximum diameter of the cutting edge of the drill.

A position of the maximum diameter of the apical portion of the thread forming section may be located offset from an apical end of the thread forming section and at a first distance from an apical end of the guide section. The first distance may be substantially equal to a second distance from said position to a coronal end of the guide surface when the thread forming tool is inserted into the guide sleeve.

The offset may be at least 1 mm, preferably at least 2 mm, for example in the range of 2-3 mm.

An apical end of the thread forming section may be larger than a maximum diameter of an apical section of the drill, which is smaller than a maximum diameter of a coronal section of the drill.

At least one of an apical section and a coronal section of the drill may be substantially cylindrical, such as circular cylindrical, tapered, or cylindrical and taped.

A diameter of the guide section of the thread forming tool may be slightly smaller than a diameter of the guide surface of the guide sleeve, such as approximately 10-200 μm, for example 30-100 μm.

The apical portion of the thread forming section may be at least partially tapering outwardly from its apical end towards its coronal end.

The combination may further comprise an implant having a bone tissue apposition surface. A maximum diameter of at least an apical portion of the bone tissue apposition surface may be smaller than or equal to a maximum diameter of the thread forming section of the thread forming tool.

The combination may further comprise an implant having a bone tissue apposition surface. A maximum diameter of an apical portion of the bone tissue apposition surface may be larger than a maximum diameter of the apical portion of the thread forming section of the thread forming tool.

The combination may further comprise an implant having a bone tissue apposition surface. A maximum diameter of a coronal portion of the bone tissue apposition surface may be larger than a maximum diameter of the entire and/or coronal portion of the thread forming section of the thread forming tool.

The thread forming section of the thread forming tool may comprise a helical thread with at least one cutting surface. The bone tissue apposition surface of the implant may comprise at least one helical thread.

In certain embodiments, a longitudinal cross-sectional shape of the helical thread of the thread forming section substantially corresponds to a longitudinal cross-sectional shape of the helical thread of the implant. The cross section may be taken along the central longitudinal axis of the thread forming tool and the implant, respectively.

A dimension of the helical thread of the thread forming section along at least a portion thereof may substantially correspond to a dimension of the helical thread of the implant along at least a portion thereof.

A pitch of the helical thread of the thread forming section may be substantially equal to a pitch of the helical thread of the implant.

According to a second aspect of certain embodiments, a method of providing threads in a recess in bone comprises positioning a surgical template having a guide sleeve with a guide surface at a surgical site, inserting a drill through the guide sleeve, drilling a recess in the bone while the drill is guided by the guide sleeve, inserting a thread forming tool into the guide sleeve, guiding a guide section of the thread forming tool with the guide surface of the guide sleeve before a thread forming section of the thread forming tool starts forming a thread in the recess, and forming a thread in the bone while the guide section of the thread forming tool is guided by the guide surface.

Further embodiments are defined in the dependent claims, features for the second aspect of certain embodiments are as for the first aspect mutatis mutandis.

Some embodiments of the disclosure provide for improved accuracy of a position of an implant in bone, for example in a position planned before the surgical intervention. Some embodiments of the disclosure provide for reducing or eliminating one or several of an angular, a vertical, a centering, and/or a lateral deviation compared to a planned position of the implant. Some embodiments of the disclosure also provide for using bone-condensing implants, such as implants tapering outwards from its apical end towards its coronal end, in guided implant surgery.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which certain embodiments of the disclosure are capable of will be apparent and elucidated from the following description of certain embodiments of the present disclosure, reference being made to the accompanying drawings, in which.

DETAILED DESCRIPTION

Figure 1A:
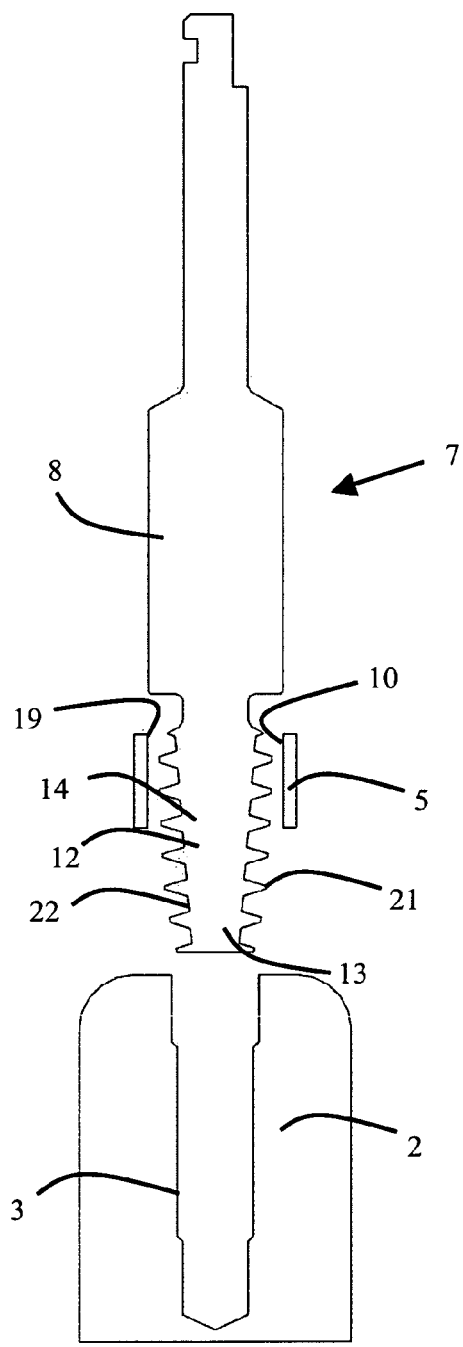
FIGS. 1a-1d are cross-sectional views of certain embodiments of a thread forming tool, a guide sleeve, and a recess formed in bone using a drill.

Specific embodiments will now be described with reference to the accompanying drawings. This disclosure may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on certain embodiments of the present disclosure applicable to guided surgery of a dental implant for placement in a jawbone. However, it will be appreciated that the invention is not limited to this application but may be applied to many other procedures, such as oral and cranio-maxillofacial implant placement in anywhere in bone in the cranium etc.

In general, certain embodiments provide for guided installation of an implant 1 in bone 2. The components and procedure according to certain embodiments have been designed such that threads accurately located in space are provided in the bone. In somewhat more detail, a recess 3 is drilled in the bone 2 using one or several drills 4a, 4b, 4c. The drill 4a, 4b, 4c may be guided by a guide sleeve 5 of a surgical template 6. A thread forming tool 7, which provides threads 3a in the bone 2, is guided by the guide sleeve 5. The thread forming tool 7 has a guide section 8, which is guided by the guide sleeve 5 before or when an apical end of the thread forming tool 7 starts forming threads in the bone 2. Hence, a very accurately located thread 3a in the bone 3 is provided. This provides for installing the implant 1 with an implant mount 9 that does not have a guide section for guidance by the guide sleeve 5. Instead, the position in space of the implant 1 is at least partially guided by the thread 3a provided in the recess 3 of the bone. For this purpose, a combination of components has been designed, which will be described in the following embodiments with reference to the examples illustrated in the figures.

FIGS. 1a-1d illustrate certain embodiments of a procedure for providing a threading in bone. The threading may comprise one or several threads 3a depending on the type of implant 1 being installed, such as an implant having a single or multiple lead thread. In the illustrated example, the bone 2 is a jawbone.

The guide sleeve 5 may be provided in the surgical template 6 as a separate or integrated component. Hence, the guide sleeve 5 may be integrated into or form part of the surgical template 6. In some embodiments, the guide sleeve is a metallic cylindrical sleeve which has been fixed to the surgical template 6, e.g. using an adhesive. In other embodiments, the guide sleeve 5 is detachable and can be inserted into a recess formed in the surgical template 6. The guide sleeve 5 has a guide surface 10 and a reference surface 11. The guide surface provides guidance to the drill 4a, 4b, 4c and/or the thread forming tool 7. Guiding in this context for certain embodiments is controlling the trajectory of the tool that is guided, such as in angular, vertical, lateral, and/or centering directions. The reference surface 11 can be used as the reference from which one or several depths or vertical directions are controlled. In the illustrated embodiment, a coronal end surface of the guide sleeve 5 serves as the reference surface. For example, the reference surface 11 has a fixed relationship relative to the planned position of the implant. Hence, by knowing the type and length of the implant 1, the depth of the recess 3 can be calculated, the correct depth drilled, and thread 3a provided at appropriate depth. The depth of any of the tooling can be controlled by markings on the tooling, such as visual or mechanical markings. A visual marking is for example a circumferential band indicating the distance to the tip of the tooling. A mechanical marking is for example a stop flange provided for abutment against the reference surface 11. The design of the guide sleeve 5 and the surgical template 6 as such is known from the NobelGuide™ planning and treatment concept mentioned above.

The thread forming tool 7 has a thread forming section 12 for forming at least one thread in bone. Also, the thread forming tool 7 comprises the guide section 8 for guidance by the guide surface 10 of the guide sleeve 5. The thread forming section 12 comprises an apical portion 13, and a coronal portion 14. The exact delimitation of the apical portion 13 and the coronal portion 14 may depend on the length of the entire thread forming section 12, which in turn may depend on the length and/or type of implant to be installed. However, in certain embodiments, a maximum diameter of the apical portion 13 of the thread forming section 12 is smaller than or equal to a maximum diameter of a cutting edge 15a, 15b, 15c of the drill 4a, 4b, 4c. When drilling the recess 3, the maximum diameter of the recess 3 will in certain embodiments correspond to the maximum diameter of the cutting edge 15a, 15b, 15c of the drill 4a, 4b, 4c. Hence, since the maximum diameter of the apical portion 13 of the thread forming section 12 is smaller than or equal to the maximum diameter of the cutting edge 15a, 15b, 15c of the drill 4a, 4b, 4c, the apical portion of the thread forming section 12 will be received within the recess 3 without condensing the bone 2 in certain embodiments. How long the apical portion 13 is received depends on the exact configuration of the apical portion 13 and the recess 3. After a certain distance, the thread forming section 12 in certain embodiments starts contacting the bone because it has a larger diameter than the recess 3, whereby threads are formed in the bone 2. By entering the thread forming section 12 in the recess 3 before the thread 3a is formed, positional control, such as centering, lateral, vertical, and/or angular control, of the thread forming section 12, is provided for in certain embodiments.

In the illustrated example, the recess 3 is stepped with a plurality of substantially circular cylindrical portions interconnected by a plurality of tapered portions. In other embodiments, the recess 3 is substantially circular cylindrical, tapered, or a combination thereof, which may be formed by a correspondingly shaped drill 4a, 4b, 4c or plurality of drills.

Figure 1B:
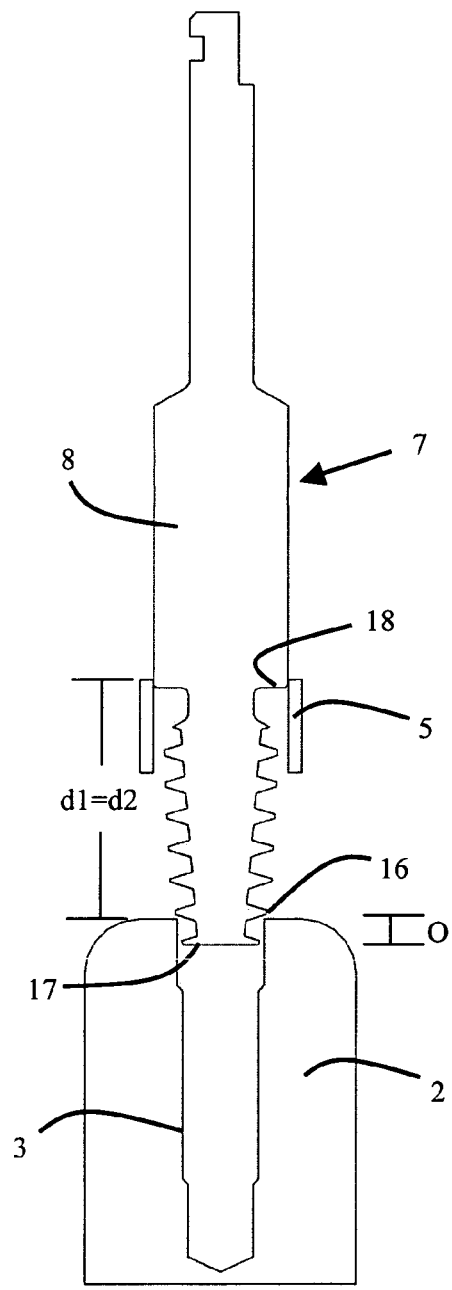

FIG. 1b illustrates an embodiment wherein a position 16 of the maximum diameter of the apical portion 13 of the thread forming section 12 is located offset O from an apical end 17 of the thread forming section 12. The position 16 is also located at a first distance d1 from an apical end 18 of the guide section 8. In the illustrated embodiment, the first distance d1 is substantially equal to a second distance d2, which is equal to the distance from the position 16 to a coronal end 19 of the guide surface 10 when the thread forming tool 7 is inserted into the guide sleeve 5. In the illustrated embodiment, the coronal end 19 of the guide surface 10 is located level with the reference surface 11. This embodiment provides for guidance by the guide sleeve 5 to the guide section 8 before the threaded section 12 engages the bone and starts generating the thread 3a in the bone 2. Hence, improved accuracy of the position of the thread 3a are provided for, such as improved angular, vertical, centering, and/or lateral control of the thread forming tool 7, and thus inherently improved accuracy of the position in space of the thread 3a in the bone 2.

In some embodiments, the offset O is at least 1 mm. In other embodiments, the offset is at least 2 mm or even at least 3 mm. The offset O may be in the range of 2-3 mm. The length of the offset O depends on the type of implant being installed and/or of the shape and dimension of the thread 3a that is to be provided in the bone 2. It may also depend on the length of the thread forming section 12.

Figure 1C:
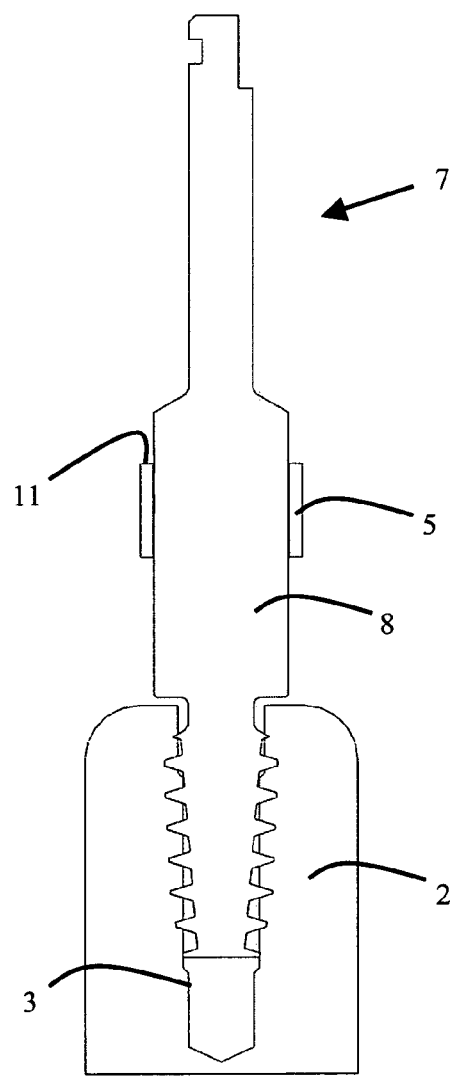
Figure 1D:
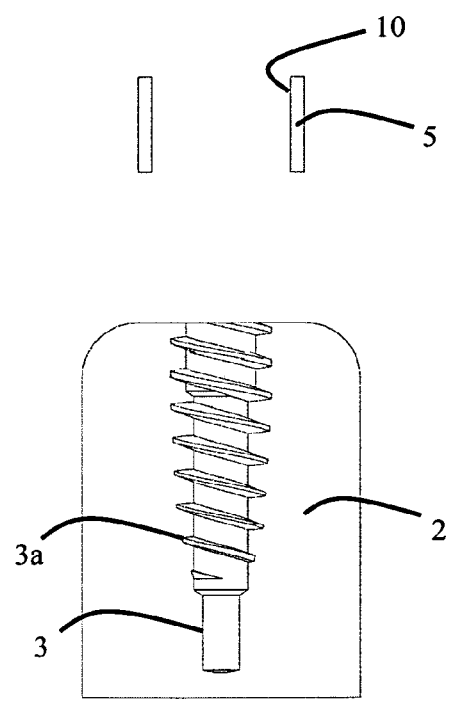

In some embodiments, the apical end 17 of the thread forming section 12 is larger than a maximum diameter of an apical section 20a, 20b, 20c of the drill 4a, 4b, 4c. In embodiments other than for a substantially cylindrical drill, the apical section 20a, 20b, 20c of the drill may be smaller than a maximum diameter of a coronal section 21 of the drill 4a, 4b, 4c, such as for stepped drill or a tapered drill. This provides for providing threads in the recess along the entire length of the thread forming section 12. However, in other embodiments, the apical end 17 of the thread forming section 12 is smaller than or equal to a diameter of the apical section 20a, 20b, 20c of the drill 4a, 4b, 4c where the apical end 17 of the thread forming tool 7 is located when it is inserted to its final depth, which is illustrated in FIG. 1c. This provides for improved stability of the implant when it is inserted, e.g. if the implant 1 has a thread cutting tip which provides threads while it is inserted to its full depth. Yet, the thread 3a provided in the coronal portion of the recess 3 controls the position of the implant 1.

In certain embodiments, a diameter of the guide section 8 of the thread forming tool 7 is slightly smaller than a diameter of the guide surface of the guide sleeve, such as approximately 10-200 μm, for example 30-100 μm. This provides for the control of the trajectory of the thread forming tool 7, as discussed above.

The apical portion 13 of the thread forming section 12 may at least partially taper outwardly from the apical end 12 towards the coronal end of the thread forming section. In the embodiments illustrated in FIGS. 1a-1c, the entire thread forming section is tapering outwardly from its apical end to its coronal end. Here, both a tip 21 and a root 22 of a thread of the thread forming section 12 when viewed in cross-section tapers, i.e. the thread gradually increases in diameter from the apical end to the coronal end. In some embodiments, the gradual increase can be interrupted and instead a section with a generally cylindrical thread at the tip 21, the root 22, and/or in-between is provided.

Figure 2A:
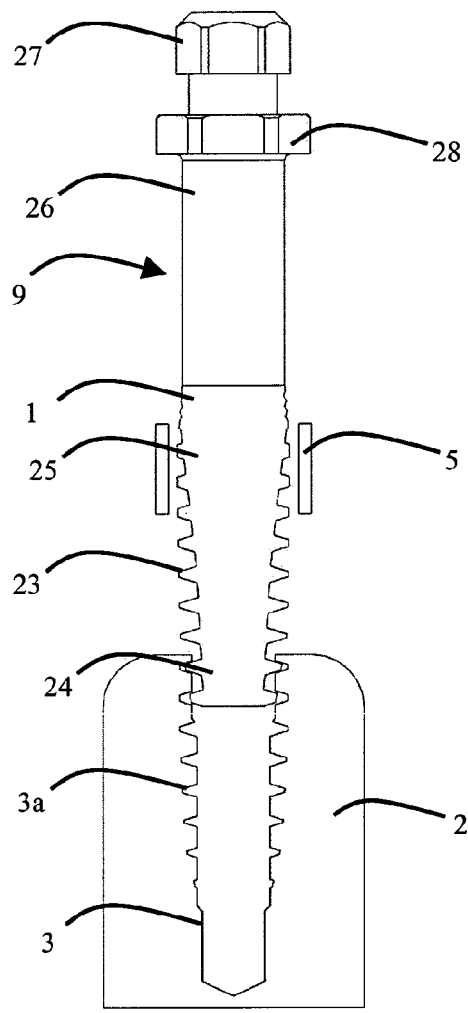
FIGS. 2a-2c are partially cross-sectional views of certain embodiments of an implant mount attached to an implant for placement into the recess in the bone at various stages of the placement procedure.
Figure 2B:
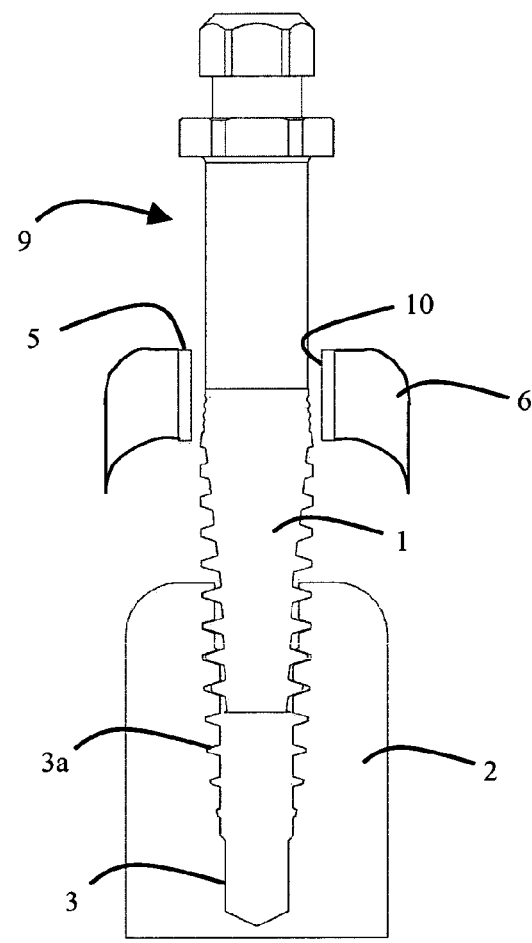
Figure 2C:
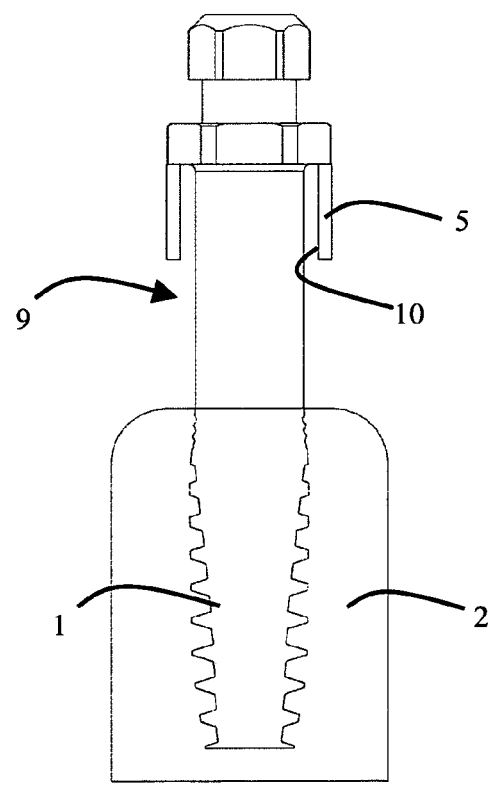

FIGS. 2a-2c illustrates the implant 1 and a procedure for placing the implant 1. The implant 1 has a bone tissue apposition surface 23, i.e. a surface that is in apposition to the bone 2 when the implant 1 is placed at its final position. For certain embodiments, a maximum diameter of at least an apical portion 24 of the bone tissue apposition surface 23 is smaller than or equal to a maximum diameter of the thread forming section 12 of the thread forming tool 7. This provides for passively threading the implant 1 into the thread 3*a* in the bone 2. Passively threading means in the context of certain embodiments that the implant can be inserted, such as by hand, to a certain depth substantially without condensing the bone. Hence there is a passive fit between the apical portion 24 of the bone tissue apposition surface 23 and the thread 3*a* in the bone 2. Hence, the thread 3 rather than the guide sleeve 5 may guide the implant, as will be discussed in more detail below. In some embodiments, it is enough if the implant can be screwed one or two full revolutions, depending on the type of thread, such as lead and/or pitch, how coarse the thread is, the number of leads, etc.

Figure 3A:
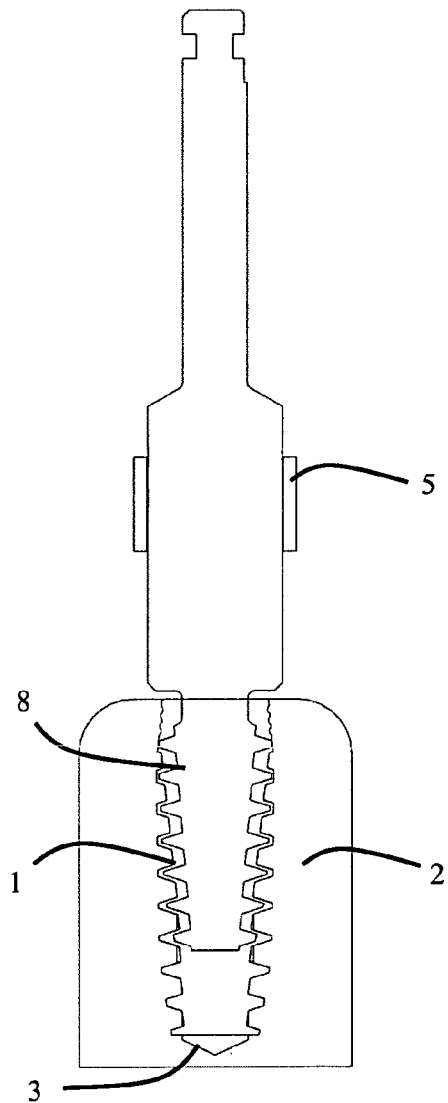
FIGS. 3a-3b are overlaid cross-sectional views of various sizes of certain embodiments of the implant and the tread forming tool.
Figure 3B:
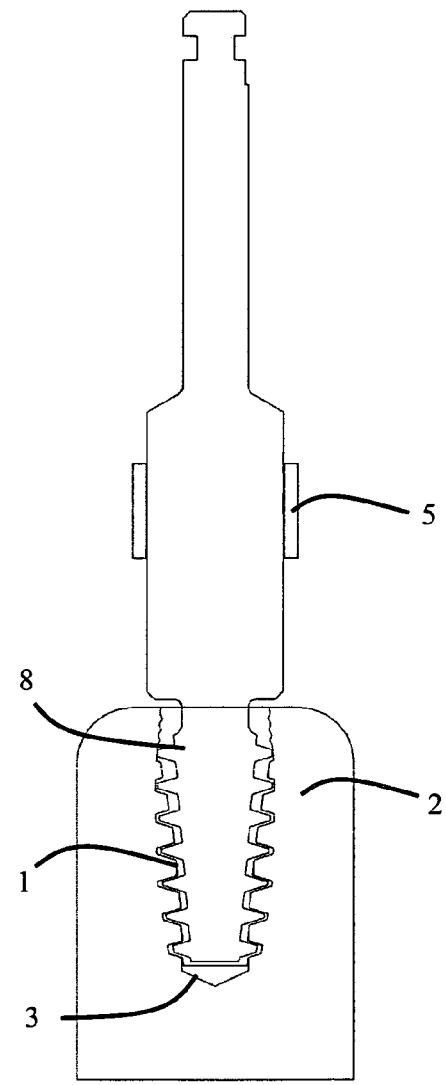

In some embodiments, a maximum diameter of the apical portion 24 of the bone tissue apposition surface 23 is larger than a maximum diameter of the apical portion 13 of the thread forming section 12 of the thread forming tool 7. This provides for improved stability of the implant, such as if the implant condenses the bone at least at the apical portion 24. This e.g. illustrated in FIG. 3*b*, wherein cross-sectional views of the thread forming tool 7 and the implant 1 are overlaid. In this embodiment, the length of the thread of the thread forming section 12 measured in the longitudinal direction of the thread forming tool 7 substantially corresponds to the length of the thread of the implant 1 measured in the longitudinal direction of the implant 1. Hence, the recess 3 is threaded substantially to its full depth. In other embodiments, such as illustrated in FIG. 3*a*, the length of the thread of the thread forming section 12 measured in the longitudinal direction of the thread forming tool 7 is shorter, such as at least 1 to 3 mm, than the length of the thread of the implant 1 measured in the longitudinal direction of the implant 1. Hence, the recess 3 is threaded only partially to its full depth. The latter embodiment provides for improved stability of the implant 1, such as if the implant condenses the bone and/or even cuts its own thread in the bone at the apical end 24.

In some embodiments, a maximum diameter of a coronal portion 25 of the bone tissue apposition surface 23 is larger than a maximum diameter of the coronal portion 14 of the thread forming section 12 of the thread forming tool 7. This provides for condensation of the bone also at the coronal region of the bone tissue apposition surface, such as to provide improved contact with cortical bone.

An embodiment of the implant mount 9 is illustrated in FIGS. 2*a*-2*c*. At one end, the implant mount 9 comprises a shank 26 with tool engaging head 27. The tool engaging head 27 has in this embodiment a hexagonal shape. Also, the implant mount has a depth indicator 28 indicating the appropriate depth of the implant. In this embodiment, the depth indicator is a tactile indicator, such as a flange, which provides tactile feedback to the user when the implant has reached its final or planner depth. The tactile feedback is e.g. provided when the flange abuts the reference surface 11 of the guide sleeve 5. Alternative, the depth indicator 28 may provide visual feedback, such as a visible marking, e.g. a circumferential band, in the shank 26.

As can be seen in the examples shown in FIGS. 2*a*-2*c*, clearance is provided between the guide surface 10 of the guide sleeve 5 and the shank 26. The guide surface 10 does not provide any guidance to the implant mount. Instead, guidance is provided by the thread 3*a* cut in the bone 2, such as lateral, centering, and/or angular guidance. This prevents that the implant mount 9 is jammed in the guide sleeve 5 and/or that the entire surgical template 6 is dislocated from its accurate position. Hence, improved positional accuracy is provided for in certain embodiments, not only for the implant 1 that is actually being installed, but also for any additional implants being installed using the same surgical template 6.

In certain embodiments, at least one of an apical section and a coronal section of the drill is substantially cylindrical, such as circular cylindrical, tapered, or cylindrical and taped.

Figures 4A, 4B, 4C:
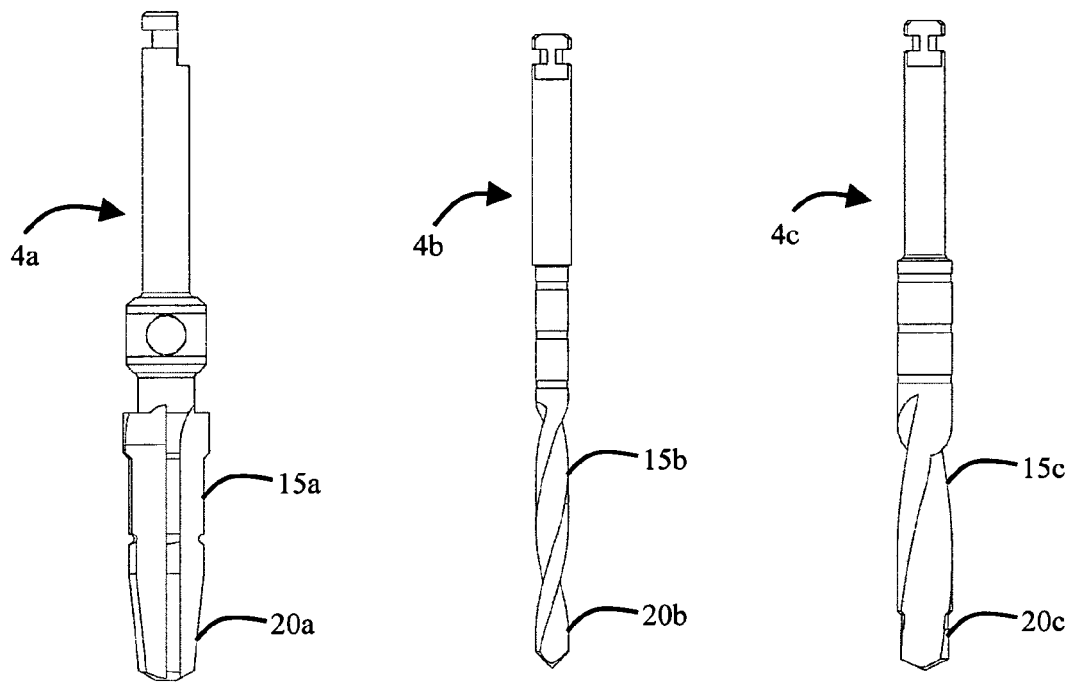
FIGS. 4a-4c are side views of certain embodiments of drills.

FIGS. 4*a*-4*c* illustrates various embodiments of drills 4*a*, 4*b*, 4*c* for forming the recess 3 in the bone 2. Each drill 4*a*, 4*b*, 4*c* has at least one cutting edge 15*a*, 15*b*, 15*c* for cutting the recess 3*a* in the bone 2.

The drill 4*a* of the embodiment of FIG. 4*a* is at least partially tapered, i.e. its cutting edge 15*a* forms substantially a circular cylinder at a coronal portion of the edge and tapered cone or truncated cone at an apical portion of the cutting edge 15*a*. The tapered portion may be in the range of 20-80% of the total length of the cutting edge 15*a* measured in the axial direction of the drill 4*a*.

The drill 4*b* of the embodiment of FIG. 4*b* is substantially cylindrical. The cutting edge 15*b* of the cylindrical drill 4*b* is helical with a constant outer diameter.

The drill 4*c* of the embodiment of FIG. 4*c* is a stepped drill, wherein the outer diameter of the cutting edge 15*c* varies along the axial direction of the drill 4*c*. The edge as such is helical. The diameter of the cutting edge relative the longitudinal central axis of the drill 4*c* at the apical portion 20*c* is smaller than the diameter of the coronal portion of the drill.

Figure 4D:
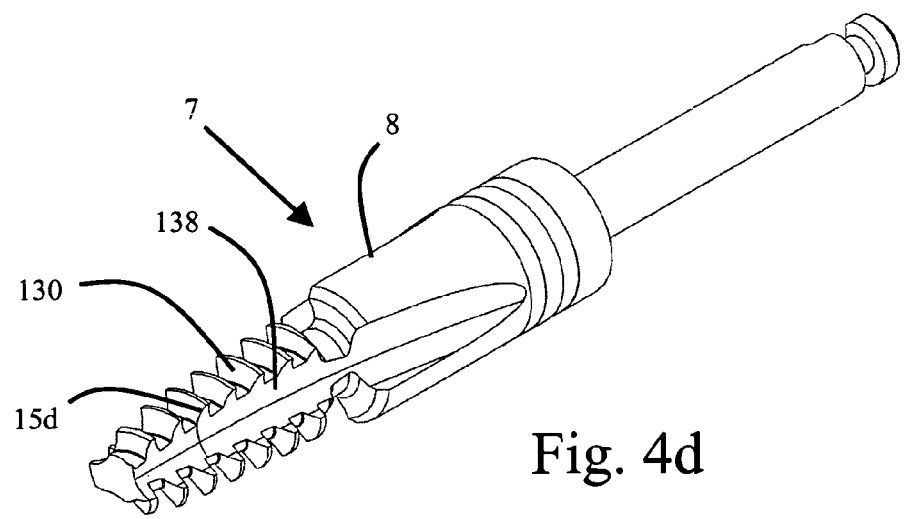
FIG. 4d is a perspective view of certain embodiments of the thread forming tool.

FIG. 4*d* illustrates an embodiment of the thread forming tool 7. The thread 130 of the thread forming tool 7 is helical and interrupted by at least one cutting surface 15*d* on each revolution of the thread 130 around the perimeter of the thread forming section. A recess 138 is formed in the thread 130 starting at the tip of the thread forming section and ends on the guiding section.

Components according to some embodiments provide for passively inserting an implant in bone at least initially when it is placed. Passively threading means in the context of certain embodiments that the implant can be inserted, such as by hand, to a certain depth without condensing the bone. The implant may contact the bone, but substantially not condense. Hence, a passive fit between the implant and the bone is provided. This provides for the implant more closely following an anticipated trajectory, i.e. is guided by the bone, and/or a more uniform condensation of the bone 2 when the implant 1 is placed.

Figure 5A:
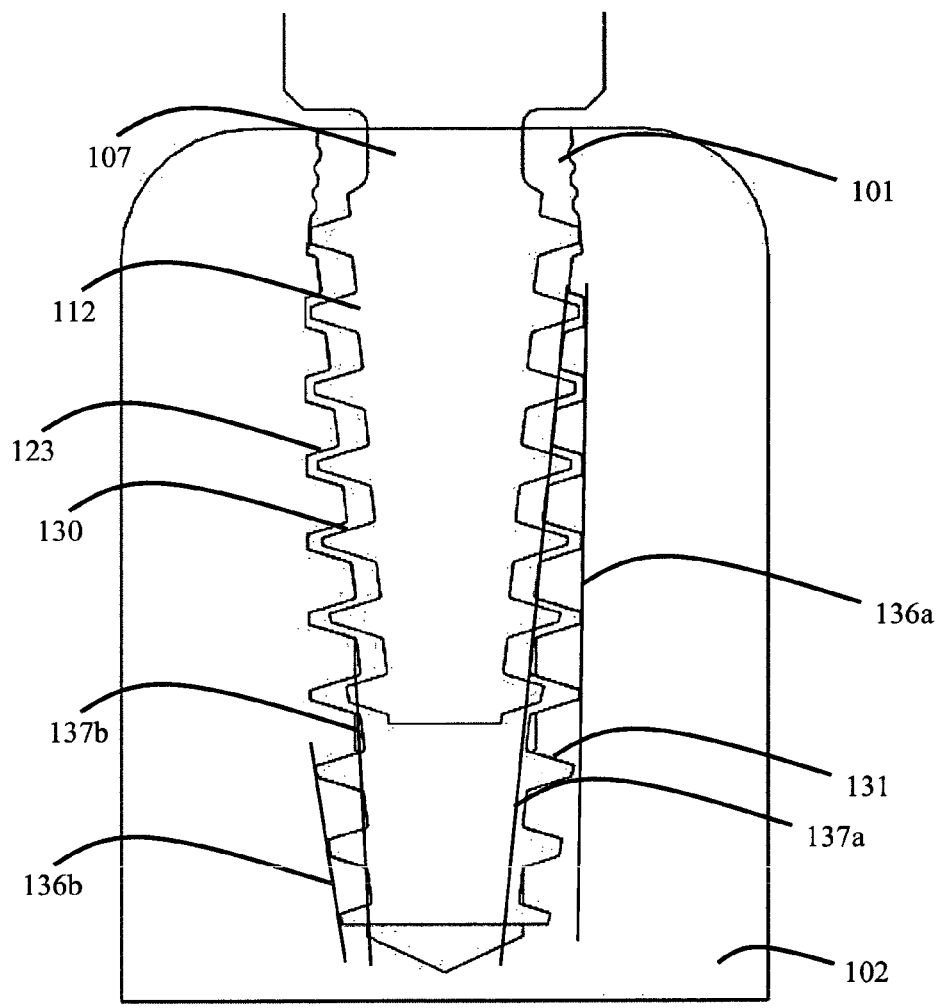
FIGS. 5a-5c are overlaid cross-sectional views of certain embodiments of the implant and the thread forming tool.
Figure 5B:
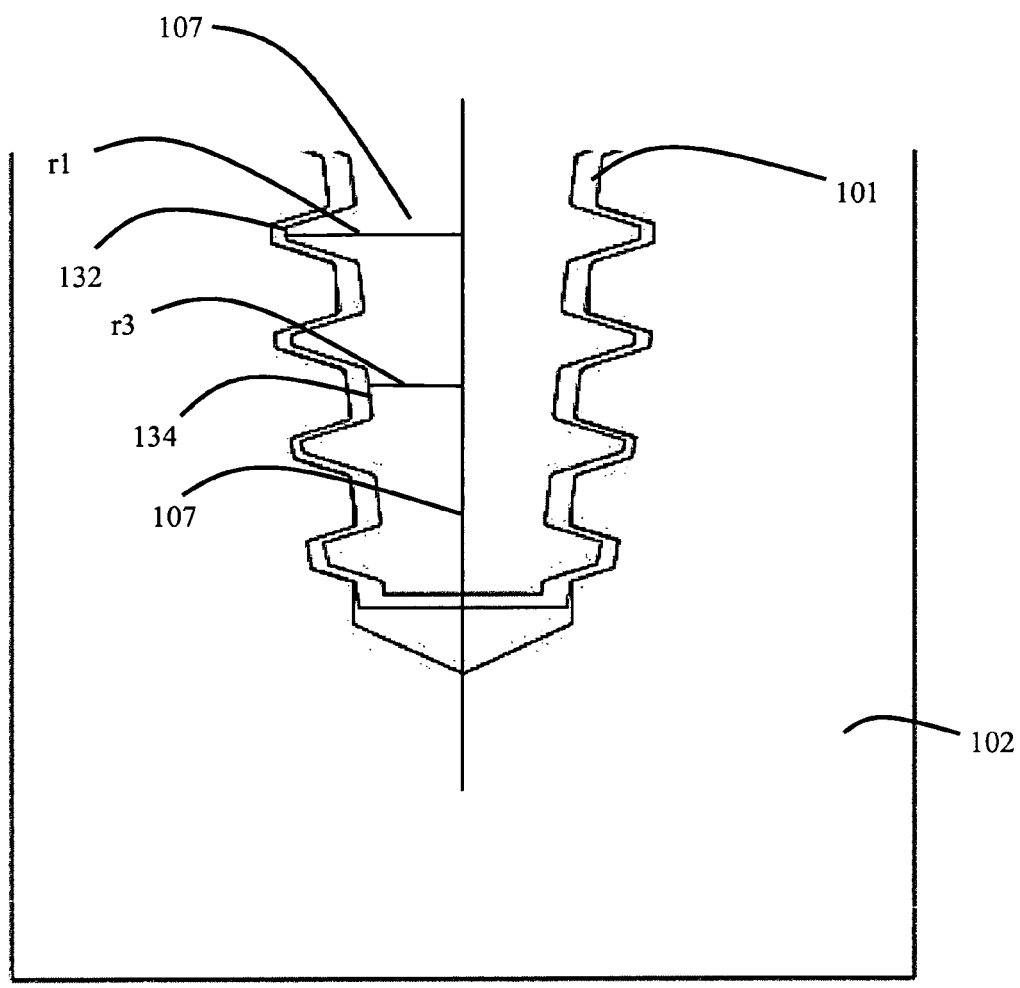
Figure 5C:
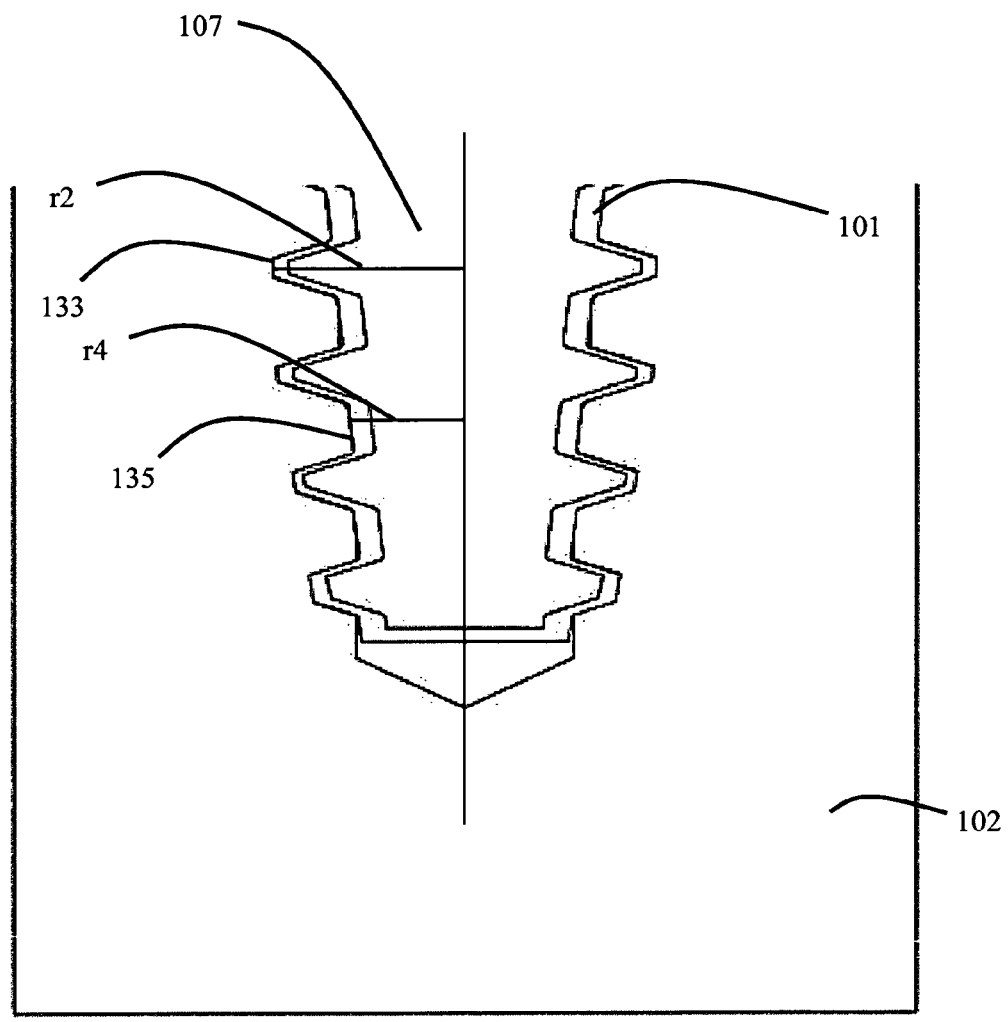

FIG. 5*a*-5*c* illustrates some embodiments, wherein longitudinal cross/sectional views of an implant 101 and a thread forming tool 107 are overlaid. The thread forming tool 107 comprises a thread forming section 112 with a helical thread 130 having at least one cutting surface for cutting a thread in bone 102. The implant 101 comprises a bone apposition surface 123 having at least one helical thread 131 for position at least partially in a thread of the bone 102. In certain embodiments, a longitudinal cross-sectional shape of at least a portion of the helical thread 130 of the thread forming section substantially corresponds to a longitudinal cross-sectional shape of at least a portion of the helical thread 131 of the implant 101. This provides for substantially uniform distribution of load from the implant 101 to the bone 103 when the implant is inserted. This may, in turn, additionally provide for a more predictable path of trajectory when the implant 101 is placed in the bone 102.

The longitudinal cross-sectional shape of the helical thread 130, 131 of the thread forming section 112 and the implant, respectively, may comprise the thread profile including the root of the thread, the tip of the thread, and the thread flank extending between the root of the thread to the tip of the thread. In the illustrated embodiment, the tip of the threads 130, 131 comprises a flat face. The flat face may vary in width in the axial direction of the thread 130, 131. Furthermore, the root of the thread 130, 131 may form a substantially flat surface having a width. The shape of the root of the thread may be constant in the axial direction of the thread. Each of the tip, root, and/or flank of the thread may comprise at least one recess in the micrometer range for promotion of osseointegration.

In some embodiments, a dimension of the cross-sectional shape of the helical thread 130 of the thread forming section 112 substantially corresponds to a corresponding dimension of the cross-sectional shape of the helical thread 131 of the implant 101. In other embodiments, the dimension of the cross-sectional shape of the helical thread 130 of the thread forming section 120 is smaller than a corresponding dimension of the cross-sectional shape of the helical thread 131 of the implant 101. The smaller the dimension is, the more condensing of the bone may be provided for. Hence, for applications in harder bone the difference of the dimensions may be smaller than for applications in softer bone.

For example, in certain embodiments, the dimension of the thread forming section 112 and the implant 101 are measured when they are aligned in a position which is their optimal final position, such as is illustrated in FIGS. 5a-5c. The dimension may then be measured at a lateral cross section of the threaded section 112 and the implant 101 which is located at the same distance from the coronal end of the implant 101. Hence, in certain embodiments, the dimensions are measured when the threaded section 112 is vertically aligned with the implant 101 and the threads 130, 131 are rotationally aligned, i.e. the threads uniformly overlap. In some embodiments, the dimension of the thread forming section 112 is a radius r1 (FIG. 5b) from the central longitudinal axis of the thread forming tool 112 to an external surface of a tip 132 of the thread 130 of the thread forming section 112. The corresponding dimension of the thread 131 of the implant 101 is a radius r2 (FIG. 5c) from the central longitudinal axis of the implant to an external surface of a tip 133 of its thread 131 for a lateral cross section taken at the same distance, as for measuring r1, from the coronal end of the implant 101.

Alternatively or additionally, the dimension of the thread forming section 112 is a radius r3 (FIG. 5b) from the central longitudinal axis of the thread forming tool 112 to an external surface of a root 134 of its thread. A corresponding dimension of the thread 131 of the implant 101 is a radius r4 (FIG. 5c) from the central longitudinal axis of the implant 101 to an external surface of a root 135 of its thread. In some embodiments, the dimensions for the root are measured in the same way as for the dimension for the tips 132, 133, as described above.

In some embodiments, a pitch of the helical thread 130 of the thread forming section 112 is substantially equal to a pitch of the helical thread 131 of the implant 101. The pitch is the distance from the crest of the thread to the next crest when the thread is viewed in longitudinal cross section. In some embodiments of the disclosure, the threads 130, 131 of the threaded section 112 and the implant 101, respectively, may be single or multiple lead threads.

In the embodiment of FIG. 5a, the thread forming section 112 is at least partially tapering outwardly from its apical end towards its coronal end. Similarly, an apical portion, such as the entire or a portion of the threaded section of the implant 101, of the implant 101 is least partially tapering outwardly from its apical end towards its coronal end. For example, either or both of the tip 133 and the root 135 of the thread 131 of the implant taper relative the central longitudinal axis of the implant 101. Alternatively, at least a portion of the tip 133 is substantially cylindrical and at least a portion of the root 135 of the thread 131 in the axial direction of the helical thread of the implant 101 taper relative the central longitudinal axis of the implant 101. In FIG. 5a, the level of taper of the tip or crest 133 of the thread 131 has been indicated by straight lines 136a, 136b interconnecting a number of tip sections along various portions of the thread along the longitudinal axis of the implant 101. Also, the level of taper of the root 135 of the thread 131 has been indicated by straight lines 137a, 137b interconnecting a number of root sections along various portions of the thread 131 along the longitudinal axis of the implant 101. As can be seen in this example, the level of taper at the coronal end of the implant 101 compared to the apical end of the implant is less for both the tip 133 and root 135. Each root section may also taper more than the general taper of a number of subsequent root sections. This provides for improved bone-condensing properties, which is described in more detail in WO2004103202 and WO2008128757, which are incorporated herein by reference in their entirety for all purposes. The thread 131 of the thread forming section 112 may have the same general taper as the thread 131 of the implant 101.

In some embodiments, a maximum diameter of at least an apical portion of the bone tissue apposition surface 123 is smaller than or equal to a maximum diameter of the thread forming section 112 of the thread forming tool 107. This provides for passively threading the implant at least to a certain extent before condensing of the bone commences. The passively threading may correspond to the offset O discussed below.

In some embodiments, a maximum diameter of an apical portion of the bone apposition surface 123 is larger than a maximum diameter of an apical portion of the thread forming section of the thread forming tool, and smaller than a coronal portion of the thread forming section of the thread forming tool. This provides for passively initial threading of the implant into the recess of the bone, and condensation of the bone at least at the apical portion of the implant 101, whereby improved stability can be obtained as well as a more controlled trajectory of the implant, as discussed above.

In some embodiments, a maximum diameter of a coronal portion of the bone tissue apposition surface is larger than a maximum diameter of a coronal portion of the thread forming section of the thread forming tool. This provides for condensation of the bone at least at the coronal portion of the implant 101, whereby improved stability can be obtained as well as a more controlled trajectory.

The length of the implant 101 from its apical to its coronal end may be in the range of 6-20 mm, such as 8-18 mm. The maximum diameter of the thread of the implant may be in the range of 1.8-5.5 mm, such as 2.5-5.0 mm. As discussed above, the length and diameter of the thread forming section of the thread forming tool may be equivalent or slightly less than the dimensions of the implant. In some situations, the length and diameter of the thread forming section of the thread forming tool may be slightly larger than the dimensions of the implant.

An embodiment of a method for forming the thread 3a in the bone 2, comprises positioning a surgical template having a guide sleeve with a guide surface at a surgical site, inserting a drill through the guide sleeve, drilling a recess in the bone while the drill is guided by the guide sleeve, inserting a thread forming tool into the guide sleeve, guiding a guide section of the thread forming tool with the guide surface of the guide sleeve before a thread forming section of the thread forming tool starts forming a thread in the recess, and forming a thread in the bone while the guide section of the thread forming tool is guided by the guide surface.

An embodiment of a method of placing an implant in a threaded recess in bone, comprises drilling a recess in bone, forming a thread in the recess having a shape which at least partially corresponds to a shape of a thread of an implant, and inserting said implant in said threaded recess.

The present invention has been described above with reference to specific embodiments. However, other embodiments than the above described are equally possible within the scope of the invention. Different method steps than those described above may be provided within the scope of the invention. The different features and steps of the invention may be combined in other combinations than those described. The scope of the invention is only limited by the appended patent claims.

What is claimed is:

1. A method of placing an implant, the method comprising:
    positioning a surgical template at a surgical site;
    positioning a guide sleeve with a guide surface in the surgical template;
    inserting a drill having a cutting edge through the guide sleeve;
    drilling a recess in the bone while the drill is guided by the guide sleeve;
    inserting a thread forming tool into the guide sleeve, wherein the thread forming tool has a thread forming section, the thread forming section having at least one thread for forming at least one corresponding thread in the bone, and a guide section, the thread forming section comprising an apical portion including the at least one thread, and a coronal portion, the thread forming tool having a maximum diameter of the at least one thread of the apical portion of the thread forming section that is smaller than or equal to a maximum diameter of the cutting edge of the drill;
    guiding the guide section of the thread forming tool with the guide surface of the guide sleeve before the thread forming section of the thread forming tool starts forming the corresponding thread in the recess;
    forming the corresponding thread in the bone while the guide section of the thread forming tool is guided by the guide surface; and
    inserting the implant in the threaded recess, wherein the implant has a bone tissue apposition surface comprising an apical portion and a coronal portion, and wherein a maximum diameter of the thread forming section of the thread forming tool is smaller than a maximum diameter of the bone tissue apposition surface of the implant.

2. The method according to claim 1, wherein inserting the implant in the threaded recess comprises inserting in the threaded recess the implant having a maximum diameter of the apical portion of the bone tissue apposition surface that is larger than a maximum diameter of the at least one thread of the apical portion of the thread forming section of the thread forming tool.

3. The method according to claim 1, wherein inserting the implant in the threaded recess comprises inserting in the threaded recess the implant having a maximum diameter of the coronal portion of the bone tissue apposition surface that is larger than a maximum diameter of the coronal portion of the thread forming section of the thread forming tool.

4. The method according to claim 1, wherein inserting the implant in the threaded recess comprises inserting in the threaded recess the implant having a maximum diameter of the apical portion of the bone tissue apposition surface that is smaller than a maximum diameter of the coronal portion of the thread forming section of the thread forming tool.

5. The method according to claim 1,
    wherein inserting the thread forming tool into the guide sleeve comprises inserting into the guide sleeve the thread forming tool having a position of a maximum diameter of the at least one thread of the apical portion of the thread forming section that is located offset from an apical end of the thread forming section and at a first distance from an apical end of the guide section; and
    wherein inserting the thread forming tool into the guide sleeve comprises inserting the thread forming tool into the guide sleeve such that the first distance is substantially equal to a second distance from said position to a coronal end of the guide surface of the guide sleeve.

6. The method according to claim 5, wherein inserting the thread forming tool into the guide sleeve comprises inserting into the guide sleeve the thread forming tool having the offset that is at least 1 mm.

7. The method according to claim 6, wherein inserting the thread forming tool into the guide sleeve comprises inserting into the guide sleeve the thread forming tool having the offset that is at least 2 mm.

8. The method according to claim 7, wherein inserting the thread forming tool into the guide sleeve comprises inserting into the guide sleeve the thread forming tool having the offset that is in a range of 2 mm to 3 mm.

9. The method according to claim 1,
    wherein inserting the thread forming tool into the guide sleeve comprises inserting into the guide sleeve the thread forming tool having an apical end of the thread forming section that is larger than a maximum diameter of an apical section of the drill; and
    wherein inserting the drill through the guide sleeve comprises inserting through the guide sleeve the drill having the apical section that is smaller than a maximum diameter of a coronal section.

10. The method according to claim 1, wherein inserting the drill through the guide sleeve comprises inserting through the guide sleeve the drill having at least one of an apical section and a coronal section that is substantially cylindrical, tapered, or cylindrical and tapered.

11. The method according to claim 1, wherein inserting the drill through the guide sleeve comprises inserting through the guide sleeve the drill having at least one of an apical section and a coronal section that is circular cylindrical.

12. The method according to claim 1, wherein inserting the thread forming tool into the guide sleeve comprises inserting into the guide sleeve the thread forming tool having a diameter of the guide section that is slightly smaller than a diameter of the guide surface of the guide sleeve.

13. The method according to claim 1, wherein inserting the thread forming tool into guide sleeve comprises inserting into the guide sleeve the thread forming tool having the apical portion of the thread forming section that is at least partially tapering outwardly from its apical end towards its coronal end.

14. The method according to claim 1,
    wherein inserting the thread forming tool into the guide sleeve comprises inserting into the guide sleeve the thread forming tool having the at least one thread of the thread forming section that comprises a helical thread with at least one cutting surface; and wherein inserting the implant in the threaded recess comprises inserting in the threaded recess the implant having the bone tissue apposition surface that comprises at least one helical thread.

15. The method according to claim 14, wherein inserting the thread forming tool into the guide sleeve comprises inserting into the guide sleeve the thread forming tool having a longitudinal cross-sectional shape of the helical thread of the thread forming section that substantially corresponds to a longitudinal cross-sectional shape of the helical thread of the implant.

16. The method according to claim 14, wherein inserting the thread forming tool into the guide sleeve comprises inserting into the guide sleeve the thread forming tool having a pitch of the helical thread of the thread forming section that is substantially equal to a pitch of the helical thread of the implant.

17. The method according to claim 14, wherein inserting the thread forming tool into the guide sleeve comprises inserting into the guide sleeve the thread forming tool having a dimension of the cross-sectional shape of the helical thread of the thread forming section that is smaller than a corresponding dimension of the cross-sectional shape of the helical thread of the implant.

18. The method according to claim 1, wherein inserting the thread forming tool into the guide sleeve comprises inserting into the guide sleeve the thread forming tool having a diameter of the guide section that is approximately 10 μm to approximately 200 μm smaller than a diameter of the guide surface of the guide sleeve.

19. The method according to claim 18, wherein inserting the thread forming tool into the guide sleeve comprises inserting into the guide sleeve the thread forming tool having a diameter of the guide section that is approximately 30 μm to approximately 100 μm smaller than a diameter of the guide surface of the guide sleeve.

\* \* \* \* \*